United States Patent
Petit et al.

[11] Patent Number: 5,939,370
[45] Date of Patent: Aug. 17, 1999

[54] FLUOROALKVIGLYCOSIDURONIC ACIDS AND CORRESPONDING 6(3)-LACTONES, PREPARATION AND USES

[75] Inventors: Serge Petit, Cusy; Stephane Fouquay, Mont-Saint Aignan; Daniel Bernard, Courbevoie, all of France

[73] Assignee: CECA S.A., France

[21] Appl. No.: 08/879,784

[22] Filed: Jun. 20, 1997

[30] Foreign Application Priority Data

Jun. 20, 1996 [FR] France .................................. 96 07693

[51] Int. Cl.$^6$ .............................. A61K 7/075; C07G 3/00
[52] U.S. Cl. ........................ 510/119; 536/4.1; 536/18.4; 536/123
[58] Field of Search ..................... 510/180, 181, 510/218, 119, 121, 130, 137, 158; 536/4.1, 123.1, 18.4

[56] References Cited

U.S. PATENT DOCUMENTS 5,728,670  3/1998  Harichian et al. ...................... 510/392

FOREIGN PATENT DOCUMENTS

93/02092  2/1993  WIPO .
95/10524  4/1995  WIPO .

OTHER PUBLICATIONS

Harry W.C. Raaijimakers et al., "The synthesis and properties of some long–chainalkyl–D–glucofuranosidurono–6, 3–lactones, D–glucofuranosides and derivatives thereof", *Recl. Tray. Chim. Pays–Bas*, vol. 113, pp. 79–87, 1994.

*Primary Examiner*—Alan L. Rotman
*Assistant Examiner*—Charanjit S. Aulakh
*Attorney, Agent, or Firm*—Millen, White, Zelano, & Branigan, P.C.

[57] ABSTRACT

The invention relates to fluoroalkyl derivatives of uronic acids of the formula:

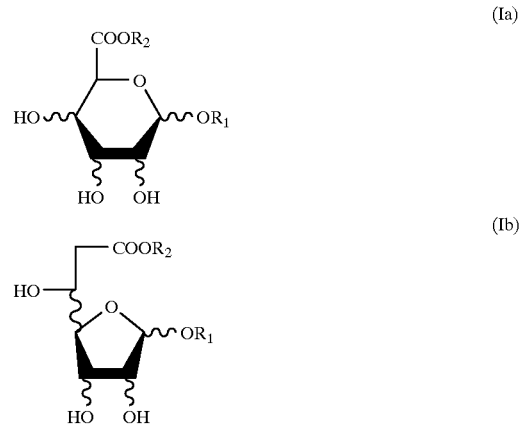

and the corresponding lactones, as well as a process for the preparation of the said compounds, which comprises reacting a glycosiduronic acid or a glycosiduronolactone with an alcohol of formula $R_1OH$, which process may also include steps of basiciation and acidification. The compounds according to the invention may be used in particular as surfactants.

10 Claims, No Drawings

FLUOROALKYLGLYCOSIDURONIC ACIDS AND CORRESPONDING 6(3)-LACTONES, PREPARATION AND USES

BACKGROUND OF THE INVENTION

The present invention relates to fluoroalkylglycosiduronic acids and the corresponding lactones, to a process for their preparation and to their uses, in particular as surfactants.

Fluoro compounds are known for their surfactant properties. The most important family of these compounds is represented by anionic derivatives of the carboxylate, sulphonate, sulphate and phosphate type.

In particular, sugar-based fluoro compounds have formed the subject of much research since they offer, inter alia, excellent compatibility with human tissues. Accordingly, their applications fall essentially in the biomedical field, where they are employed to form fluorocarbon vesicles or emulsions which act as blood substitutes, contrast agents or vectorization agents and agents for the controlled release of medicinal products.

The prior art in this field includes in particular:

the article by J. G. Riess and J. Greinier [Carbohydrates as Organic Raw Materials II, pp. 209–259, published by VCH (1993)] which describes fluoroalkyl sugars comprising a hydrophilic head of lucidic nature, a junction component (for example ester, ether, amide or phosphoester), a hydrocarbon spacer and a perfluoroalkyl tail;

patent applications WO-A-92/05444 and WO-A-92/05445 which describe a reactant intended to immobilize a biomolecule on a solid or liquid fluorocarbon support. This reactant contains, on the one hand, fluoroalkyl groups which allow binding to the support, and, on the other hand, a reactive group on the anomeric carbon which is necessary for covalent coupling with the biomolecule;

application WO-A-92/21688 which describes perfluoroalkyl and phosphorus-containing amphiphilic molecules containing in particular a radical derived from a sugar;

and application WO-A-94/03468 which discloses amphiphilic molecules containing a polyhydroxylated hydrophilic part, in particular a mono- or oligosaccharide, a hydrophobic part, for example a fluorocarbon part, and a component for joining the said parts together, which is derived from an amino acid or a peptide.

Moreover, it is known that glycosiduronic acid derivatives are surfactants of high performance which are well tolerated by the skin and the mucous membranes. Such compounds are described, for example, in EP-A-550,276, EP-A-537,820, EP-A-532,370 and P-A-05-170,642. However, it is not taught that the abovementioned compounds can contain one or more fluoroalkyl radicals.

SUMMARY OF THE INVENTION

It has now been found that fluoro derivatives of glycosiduronic acids have surfactant properties. The present invention thus relates to perfluoroalkylglycosiduronic acids and derivatives thereof, as well as to the corresponding lactones.

Another subject of the invention relates to a process for the preparation of the abovementioned acids and lactones by grafting of a fluoroalkyl chain (glycosylation and, where appropriate, esterification). In contrast with the processes of the prior art mentioned above which involve steps of protection and deprotection of the hydroxyl groups, the present process involves an unprotected substrate.

Another subject of the invention relates, lastly, to the use of the said acids and lactones as surfactants.

More precisely, the perfluoroalkylglycosiduronic acids and derivatives thereof of the present invention have the formula:

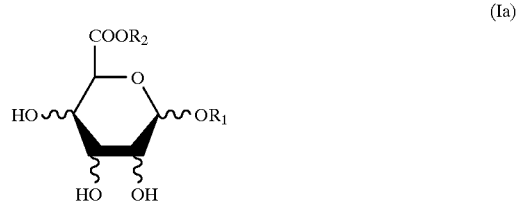

(Ia)

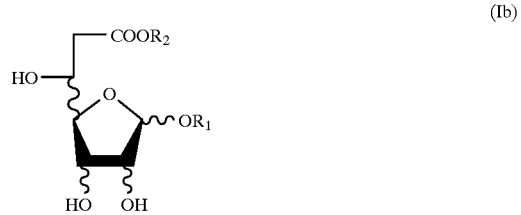

(Ib)

in which:

$R_1$ represents a saturated or unsaturated, linear or branched fluoroalkyl radical containing 4 to 46 carbon atoms;

$R_2$ represents H, $R_1$ as defined above, an alkali metal or alkaline-earth metal, or a quaternary ammonium of formula:

in which $R_3$, $R_4$, $R_5$ and $R_6$, which may be identical or different, represent H or a $C_1$–$C_6$ alkyl or hydroxyalkyl radical.

$R_1$ preferably has the formula:

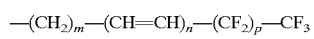

$-(CH_2)_m-(CH=CH)_n-(CF_2)_p-CF_3$ in which:

m is between 2 and 22, n is equal to 0 or 1, p is between 1 and 21.

The lactones corresponding to the fluoroalkylglycosiduronic acids, which are also a subject of the present invention, have the formula:

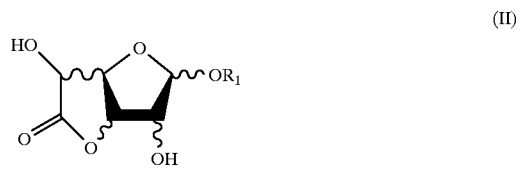

(II)

in which $R_1$ has the meaning given above.

The preferred lactones are fluoroalkyl-6(3)-glucofuranuronolactone and fluoroalkyl- 6(3)-mannofuranuronolactone, fluoroalkyl-6 (3)-idofuranuronolactone, fluoroalkyl-6 (3)

-gulofuranuronolactone and, better still, fluoroalkyl-6(3)-D-glucofuranuronolactone, fluoroalkyl-6(3)-D-mannofuranuronolactone, fluoroalkyl-6(3)-L-idofuranuronolactone and fluoroalkyl-6(3)-L-gulofuranuronolactone.

The fluoroalkylglycosiduronic acids and the derivatives thereof, as well as the corresponding lactones, may be prepared according to the process which consists in reacting a glycosiduronic acid or a glycosiduronolactone with an alcohol of formula $R_1OH$ in which $R_1$ has the meaning given above, in the presence of an acidic catalyst, in recovering the hydrogen fluoroalkylglycosiduronate, its derivatives or the corresponding lactone, and, where appropriate, in using a base in order to obtain the fluoroalkylglycosiduronic acid salt.

The process according to the invention will be better understood in the light of the explanations which follow.

Preparation of fluoroalkyl fluoroalkylglycosiduronates ($R_2=C_4-C_{46}$ fluoroalkyl) and fluoroalkylalycosiduronolactone The process consists in reacting:

1 molar equivalent of a glycosiduronic acid or of a glycosiduronolactone;

1 to 25 molar equivalents of an alcohol of formula $R_1OH$, $R_1$ having the meaning given above, preferably 1 to 3 equivalents when an additional solvent is used and 3 to 25 equivalents when no additional solvent is used;

0.01 to 2 molar equivalents of an acidic catalyst or 0.05 to 6 equivalents by weight of a resin or a clay which is acidic.

The glycosiduronic acid is generally chosen from uronic acids containing 5 or 6 carbon atoms, such as riburonic acid, arabinuronic acid, xyluronic acid, lyxuronic acid, glucuronic acid, galacturonic acid, mannuronic acid, iduronic acid, guluronic acid, alluronic acid, talluronic acid and altruronic acid. Glucuronic acid, galacturonic acid, mannuronic acid, iduronic acid or guluronic acid is preferably used, and better still glucuronic acid or galacturonic acid.

The glycosiduronolactone is generally chosen from the lactones of the abovementioned glycosiduronic acids. By way of example, mention may be made of 6(3)-glucuronolactone, 6(3)-mannuronolactone, 6(3)-guluronolactone and 6(3)-iduronolactone.

6(3)-Glucuronolactone and 6(3)-mannuronolactone are preferably used.

The additional solvent which may be used in the process according to the invention is generally chosen from oxide ethers such as tetrahydrofuran and ethylene glycol dimethyl ether, halogenated ydrocarbons such as dichloromethane, dichloroethane and chloroform, esters such as ethyl, propyl or butyl acetate, alcohols such as methanol, ethanol, propanol or butanol, amides such as N-methylformamide or N,N-dimethylformamide, and mixtures of these compounds.

The additional solvent is generally used in a proportion of from 0 to 20 equivalents by weight per one equivalent by weight of starting glycosiduronic acid or of starting glycosiduronolactone.

The catalyst is generally chosen from acids such as hydrochloric acid or sulphuric acid, alkylsulphuric acids such as decyl- or laurylsulphuric acid, sulphonic acids such as benzenesulphonic acid, para-toluenesulphonic acid or camphorsulphonic acid, alkylsulphonic acids such as methanesulphonic acid, decylsulphonic acid or laurylsulphonic acid, sulphosuccinic acids, alkyl sulphosuccinates such as decyl or lauryl sulphosuccinate, perhalohydric acids such as perchloric acid or hypophosphorous acid, and mixtures of these acids. Sulphuric acid, an alkylsulphuric acid, methanesulphonic acid, sulphosuccinic acid, an alkyl sulphosuccinate and hypophosphorous acid are preferably used.

The catalyst may also be chosen from metals such as copper and iron, metal oxides, metal salts such as halides, halogens such as iodine, antimony pentahalides such as the pentachlorides or pentafluorides, and titanium sulphates.

The resin is generally chosen from resins in $H^+$ form, for example sulphonic resins.

The acidic resin and the acidic clay also have a high capacity for water retention. As such, they are preferred when a dehydrating effect is desired. They may be used alone or mixed with a standard dehydrating agent, for example molecular sieves or a zeolite.

The process is generally carried out at a temperature of between 50 and 20° C., preferably 70 and 150° C., and for a period which may range from one hour to three days, preferably 1 to 24 hours.

The reaction is generally carried out at a pressure of between 0.013 and 101.325 kPa and preferably between 0.013 and 4 kPa.

After the reaction, a step of removal of the catalyst is carried out, which may be performed in two ways depending on the nature of this catalyst.

When the catalyst is an acid (catalysis in homogeneous medium), it is neutralized, for example, using a bicarbonate of an alkali metal such a sodium or potassium, and the salt formed is removed by filtration or by precipitation in water and washing of the precipitate with water, where appropriate a solvent chosen from the abovementioned additional solvents, preferably an alkane or an oxide ether.

When the catalyst is a resin or a clay (heterogeneous catalysis), it is removed by conventional filtration.

After the said step of removal of the catalyst and, where appropriate, of the excess alcohol, the fluoroalkyl fluoroalkylglycosiduronate or the fluoroalkylglycosiduronolactone is recovered.

These compounds usually consist of a mixture of the pyran and furan forms which may be separated, for example, by chromatography on a column of silica.

Preparation of fluoroalkylclycosiduronic acid salts ($R_2$=alkali metal, alkaline-earth metal or quaternary ammonium)

The process for preparing these compounds consists in reacting:

one molar equivalent of fluoroalkyl fluoroalkylglycosiduronate obtained according to the mode of preparation described above;

0.5 to 10 molar equivalents, preferably 1 to 3 equivalents, of a base.

The base used is generally chosen from carbonates and bicarbonates, for example of an alkali metal such as sodium or potassium, compounds of formula $M(OH)_x$ in which M represents an alkali metal or alkaline-earth metal and x is the valency of the metal, basic aluminas and quaternary ammonium hydroxides of formula:

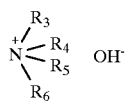

in which $R_3$, $R_4$, $R_5$ and $R_6$, which may be identical or different, have the meaning given above.

Sodium hydroxide, potassium hydroxide, aqueous ammonia or an alkyl(hydroxyalkyl)ammonium hydroxide is preferably used.

The process may also use other constituents, such as:

a solvent (0 to 20 equivalents by weight per one equivalent by weight of glycoside employed) chosen from water, alkanes such as pentane, hexane, heptane and octane, oxide ethers such as tetrahydrofuran, dioxane and ethylene glycol dimethyl ether or diethylene glycol dimethyl ether, halogenated hydrocarbons such as dichloromethane, chloroform and dichloroethane, short-chain alcohols such as methanol, ethanol, propanol, isopropanol and butanol, or longer-chain (up to 14 carbon atoms) alcohols such as octanol, decanol, dodecanol and tetradecanol and mixtures of these solvents.

Water, pentane, hexane, heptane, tetrahydrofuran, methanol, ethanol and isopropanol are preferably used.

a phase transfer catalyst (0 to 1% by weight per 1 equivalent of glycoside employed), for example a nonionic, cationic or anionic surfactant, in particular amines and compounds containing ammonium of phosphonium ions, a crown ether, a cryptand, an amino polyether, a phosphoryl sulphoxide and a glycol ester or sorbitan ester.

By way of example of compounds of ammonium type, mention may be made of hexadecyltrimethylammonium chloride, tetrabutylammonium bromide or chloride, benzyltrimethylammonium chloride, trioctylammonium chloride, tricaprylmethylammonium chloride and tetrabutylammonium hydrogen sulphate.

Hexadecyltrimethylammonium chloride and tetrabutylammonium bromide or chloride are preferably used.

The process is generally carried out at a temperature of between 0 and 100° C., preferably 0 and 60° C., and for a period which may range from 15 to 360 minutes, preferably between 15 and 120 minutes.

After the reaction, optionally after removal of the alcohol formed and the solvent, the fluoroalkylglycosiduronic acid salt is recovered.

The salt may, where appropriate, be washed with a solvent chosen from the abovementioned reaction solvents, and dried. It may also undergo a treatment intended to remove any undesirable coloration, for example using an active charcoal or an absorbent resin.

Preparation of fluoroalkylalycosiduronic acids ($R_2$=H)

The process consists in acidifying the fluoroalkylglycosiduronic acid salt, obtained according to the mode of preparation described above, with an acid.

By way of example of such an acid, mention may be made of hydrochloric acid, sulphuric acid, a sulphonic acid or a sulphonic resin in $H^+$ form.

1 to 1.2 molar equivalents are generally used per one molar equivalent of starting glycoside.

The compounds according to the invention have dispersing, wetting, foaming, emulsifying, cleansing and solubilizing properties which allow them to be used as surfactants.

These compounds may be used in particular as detergents or detergence adjuvants, for example in compositions for washing floors and windows, and for cleaning electronic components.

They may also form part of hair treatment compositions and shampoos and conditioners. On account of their emulsifying, lubricating and/or oleophobic properties, they may be used in cosmetology to prepare beauty milks, creams and ointments. In addition, their foaming and softening power is of value for the production of foam baths.

The compounds according to the invention may be incorporated in the preparation of oral hygiene products such as toothpastes and lotions for use before and after brushing the teeth.

The wetting properties may be exploited in he antimisting or antistatic treatment and polishing of various materials, for example glass, metal and plastics.

The compounds according to the invention are of value in the preparation of flame-retardant foam and powder compositions.

They may also be incorporated into adhesives based on water or on organic solvents, surface coatings such as paints and varnishes, cements and lubricating greases or waxes.

The compounds of the invention may be used in varied fields, where they may act as:

chromic bath additives, impermeabilizing additives in particular paper, photographic emulsion additives, polymer additives, in particular for preparing plastic films;

replacements for mercury in batteries with a zinc anode;

dispersion polymerization agents or emulsion polymerization agents, in particular chlorocarbon or fluorocarbon compounds, and may be involved in electrochemical processes;

liquid crystals which may be used in electrooptics or in pharmacy for the formation of lamellar phases, vesicles or capsules allowing active principles to be stabilized and vectorized, and oxygen carriers in compositions for biomedical use.

In the examples which follow, the analysis methods below are used:

Nuclear magnetic resonance (NMR)

The chemical shifts are expressed in ppm and the coupling constants J in Hz.

$^1$H NMR: performed at 300 MHz in the presence of acetone-$d_6$ containing 5% by weight of $D_2O$ (examples 1, 4 and 7-βanomer) or $CDCl_3$ (example 9), or at 200 MHz in the presence of acetone-$d_6$ containing 5% by weight of $D_2O$ (example 7- α anomer).

$^{13}$C NMR: performed at 300 MHz in the presence of acetone-$d_6$ (examples 1, 4 and 7) or at 250 MHz in the presence of $CDCl_3$ (example 9).

Infrared (IR) spectrography; 1% KBr disc

The values are expressed in $cm^{-1}$.

The Rf is measured by thin layer chromatography on silica (film thickness: 200 $\mu$m; particle size: 5–$\mu$m). The migration solvent is a 9/5 (v/v) chloroform/methanol mixture (Example 9) or ethyl acetate (Example 12). The migration spots are detected by spraying with 50% by volume sulphuric acid in water and heating at 120° C. for 2 minutes.

Surface tension (γCMC): measured at 25° C. using a Lauda tensiometer according to the stirrup tear method (ISO standard 304) using an aqueous solution in double-distilled water. The results are expressed in mN/m. The reference compound used is a polyfluoroalkyl-betaine (Forafac 1157 marked by Elf Atochem S.A.).

Critical micelle concentration (CMC): measured according to ISO standard 4311. The results are expressed in g/l.

EXAMPLE 1

Preparation of 2-(perfluorohexyl)ethyl 6(3)-D-glucofuranuronolactone 8.8 g (50 mmol) of 6(3)-D-glucuronolactone (85, 145-0; Aldrich), 109.2 g (300 mmol) of 2-(perfluorohexyl)ethanol (Foralkyl EOH 6; Ceca S. A.) and 0.24 g (2.5 mmol) of methanesulphonic acid are introduced into a 500 ml three-necked round-bottomed flask.

After 6 hours at 95° C. under a vacuum of 13.33 kPa, the reaction medium, which has become homogeneous, is cooled to 20° C., neutralized with $NaHCO_3$ and filtered. The filtrate is recovered and concentrated at 90° C. under vacuum (0.11 kPa). The viscous residue thus obtained (30 g) is dissolved in 6 ml of ethyl acetate to obtain a fluid oil (35.5 g) which is chromatographed on a column (silica 230–400 mesh ASTM; eluent: 65/35 (v/v) ethyl acetate/hexane). 9.2 g of 2-(perfluorohexyl)ethyl-6(3)-β-D-glucofuranuronolactone (Rf=0.3) and 1 g of 2-(perfluorohexyl)ethyl-6(3)-β-D-glucofuranuronolactone (Rf=0.5) are recovered, i.e. a yield, calculated on the basis of the starting 6(3)-D-glucuronolactone, equal to 35% and 3.8% respectively.

The characteristics of the lactones obtained are given below:

|  | α anomer | β anomer |
|---|---|---|
| $^1$H NMR | | |
| H1 | 5.30; d | 5.10; s |
|  | $J_{H1H2} = 4.56$ | $J_{H1H2} < 1.5$ |
| H4 | 4.84; m | 4.98; dxd |
|  |  | $J_{H4H5} = 6.37$ |
|  |  | $J_{H4H3} = 4.74$ |
| H3 | 4.77; m | 4.84; d |
|  |  | $J_{H3H4} = 4.74$ |
|  |  | $J_{H3H2} < 1$ |
| H5 | 4.62; d | 4.55; d |
|  | $J_{H5H4} = 5.23$ | $J_{H5H4} = 6.37$ |
| H2 | 4.27; dxd | 4.23; s |
|  | $J_{H1H2} = 4.56$ | $J_{H2H1} < 1.5$ |
|  | $J_{H2H3} < 1$ | $J_{H2H3} < 1$ |
| —C$\underline{H}_2$—O— | 4.20–4.10; m and | 4.20–4.10; m and |
|  | 4.00–3.90; m | 3.74–3.64; m |
| —C$\underline{H}_2$—CH$_2$—O— | 2.80–2.55 | 2.70–2.20; m |
| $^{13}$C NMR | | |
| C=O | 175.25 | 175.54 |
| C1 | 104.13 | 109.68 |
| C2 | 85.41 | 83.97 |
| C3 | 77.39 | 79.29 |
| C4 | 77.87 | 78.87 |
| C5 | 70.58 | 70.11 |
| —C$\underline{H}_2$—O— | 61.45 and 61.54 | 60.25 and 60.12 |
| —CF$_2$—C$\underline{H}_2$— | 32.23–31.39 | 32.13–31.71 |
| IR | | |
| δCH$_2$ | 2963 | 2933 |
| γC=O | 1768 | 1805, 1777 and 1756 |
| γ-OH | 3398 | 3403 |

EXAMPLE 2

Preparation of sodium 2-(perfluorohexyl)-ethyl-β-D-glucofuranuronate

To 1 g (1.9 mmol) of 2-(perfluorohexyl)-ethyl-6(3)-β-D-glucofuranosiduronolactone of Example 1 dissolved in 10 ml of absolute ethanol is added caustic soda solution portionwise until a pH equal to 12 is obtained.

After stirring for 2 hours at a temperature of 20° C., the precipitate formed is filtered off, washed with absolute ethanol and dried.

0.8 g of sodium 2-(perfluorohexyl)ethyl-β-D-glucofuranuronate is obtained, i.e. a yield, calculated on the basis of the starting lactone, equal to 74%.

EXAMPLE 3

Preparation of potassium 2-(perfluorohexyl)-ethyl-β-D-glucofuranuronate

The process is performed under the conditions of Example 2, modified in that the caustic soda solution is replaced with 3N potassium hydroxide solution.

The potassium 2-(perfluorohexyl)ethyl-β-D-glucofuranuronate obtained has a surface tension and a CMC which are respectively equal to 22 mN/m (control=16 mN/m) and 10 g/l.

EXAMPLE 4

Preparation of 2-(-perfluorohexyl)ethyl-6(3)-D-glucofuranuronolactone 12 g (68 mmol) of 6(3)-D-glucuronolactone (85, 145-0; Aldrich), 39 g (84 mmol) of 2-(perfluorooctyl)ethanol (Foralkyl EOHB; Ceca S. A.), 50 ml of diglyme and 1.2 g (12.5 mmol) of methane-sulphonic acid are introduced into a 500 ml three-necked round-bottomed flask.

After 6 hours at 110° C. under a vacuum of 13.33 kPa, the reaction medium is cooled to 20° C., neutralized with $NaHCO_3$ and stirred in the presence of 200 ml of distilled water.

The precipitate thus formed is filtered off, washed with water (50 ml×2) and with hot hexane (60 ml×3).

The brown solid recovered (28 g, i.e. a crude yield of 66% is dissolved in 7 ml of ethyl acetate and then chromatographed on a column of silica (230–400 mesh ASTM; eluent: 70/30 (v/v) ethyl acetate/hexane-ethyl acetate gradient).

The fractions corresponding to each of the α and β anomers are combined and concentrated under vacuum. The weight ratio of the α anomer to the β anomer is equal to 4/15.

The characteristics of the α and β anomers of 2-(perfluorooctyl)ethyl-6(3)-D-glucofuranuronolactone are given below.

|  | α anomer | β anomer |
|---|---|---|
| $^1$H NMR | | |
| H1 | 5.32; d | 5.12; s |
|  | $J_{H1H2} = 4.49$ | $J_{H1H2} < 1.5$ |
| H4 | 4.85; m | 5.01; dxd |
|  |  | $J_{H4H5} = 6.52$ |
|  |  | $J_{H4H3} = 4.64$ |
| H3 | 4.77; m | 4.86; d |
|  |  | $J_{H3H4} = 4.64$ |
|  |  | $J_{H3H2} < 1$ |
| H5 | 4.65; m | 4.57; d |
|  |  | $J_{H5H4} = 6.52$ |
| H2 | 4.27; m | 4.26; s |
|  |  | $J_{H2H1} < 1.5$ |
|  |  | $J_{H2H3} < 1$ |
| —C$\underline{H}_2$—O— | 4.15–4.00 and | 4.23–4.10 and |
|  | 4.00–3.85 | 3.77–3.75 |
| —C$\underline{H}_2$—CH$_2$—O— | 2.80–2.30 | 2.67–2.30 |
| $^{13}$C NMR | | |
| C=O | 175.29 | 175.70 |

-continued

|  | α anomer | β anomer |
|---|---|---|
| C1 | 104.17 | 109.80 |
| C3 | 85.44 | 84.10 |
| C2 | 77.43 | 79.42 |
| C4 | 77.99 | 79.00 |
| C5 | 70.62 | 70.23 |
| —CH$_2$—O— | 61.57 and 61.48 | 60.23 |
| —CF$_2$—CH$_2$— | 32.26–31.43 | 32.25–31.40 |
| IR | | |
| δCH$_2$ | 2981–2872 | 2944 |
| γC=O | 1800–1741 | 1805, 1778 and 1757 |
| γ-OH | 3408 | |

EXAMPLE 5

Preparation of sodium 2-(perfluorooctyl)-ethyl-β-D-glucofuranuronate

To 6 g (9.6 mmol) of 2-(perfluorooctyl)-ethyl-6(3)-β-D-glucofuranuronolactone of Example 4 dissolved in 150 ml of 96% ethanol is added, with stirring and at 25° C., 2.86N sodium hydroxide solution until a pH equal to 12 is obtained.

After stirring for 3 hours at 25° C. and partial concentration of the suspension under vacuum, the precipitate formed is filtered off and washed twice with 20 ml of absolute ethanol.

4 g of sodium 2-(perfluorooctyl)ethyl-β-D-glucofuranuronate are recovered, i.e. a yield, calculated on the basis of the starting lactone, equal to 62%.

EXAMPLE 6

Preparation of potassium 2-(perfluorooctyl)-ethyl-β-D-glucofuranuronate

The process is performed under the conditions of Example 5, modified in that the sodium hydroxide is replaced with 3N potassium hydroxide.

The potassium 2-(perfluorooctyl)ethyl-β-D-glucofuranuronate obtained has a surface tension and a CMC which are respectively equal to 21 mN/m (control=16 mN/m) and 1.2 g/l.

EXAMPLE 7

Preparation of 11-(perfluorooctyl)undecyl-6(3)-D-glucofuranuronolactone 8 g (45 mmol) of 6(3)-D-glucuronolactone (85, 145-0; Aldrich), 32.8 g (55 mmol) of 11-(perfluorooctyl)undecanol (Ceca S. A.), 40 ml of diglyme and 0.9 g (9.35 mmol) of methanesulphonic acid are introduced into a 250 ml three-necked round-bottomed flask.

After 8 hours at 110° C. under a vacuum of 13.33 kPa, the reaction medium is cooled to 25° C., 200 ml of deionized water are added and the mixture is stirred vigorously for one hour.

The precipitate thus formed is filtered off and washed with deionized water (100 ml×2) and with ethyl ether (100 ml×3).

The solid recovered (20 g, i.e. a yield of 58.8%) is a mixture of the a α and β anomers of 11-(perfluorooctyl) undecyl-6(3)-D-glucofuranuronolactone. After separation by column chromatography (silica 230–400 mesh ASTM; eluent: 70/30 (v/v) ethyl acetate/hexane), the following are recovered:

8 g of the β anomer (23.5% yield)

0.7 g of the α anomer (0.9% yield) and 5.1 g of a mixture of the α and β anomers (15% yield)

The characteristics of the α and β anomers are given below.

|  | α anomer | β anomer |
|---|---|---|
| $^1$H NMR | | |
| H1 | 5.21; d | 5.03 |
|  | $J_{H1H2}$ = 4.49 | $J_{H1H2}$ < 1.5 |
| H4 | 4.90–4.70; m | 4.95 |
|  |  | $J_{H4H5}$ = 6.0 |
| H3 | 4.90–4.70; m | 4.80 |
|  |  | $J_{H3H4}$ = 4.6 |
|  |  | $J_{H3H2}$ < 1 |
| H5 | 4.60; m | 4.51; d |
| H2 | 4.20; m | 4.23 |
|  |  | $J_{H2H1}$ < 1.5 |
|  |  | $J_{H2H3}$ < 1 |
| —CH$_2$—O— | 3.90–3.70 | 3.84–3.70 and |
|  |  | 3.36–3.24 |
| —CH$_2$—CH$_2$—O— | 3.45–3.65 | 2.40–2.10 |
| Alkyl chain | 1.80–1.40 and 1.30 | 1.70–1.40 and 1.3 |
| $^{13}$C NMR | | |
| C=O | 175.00 | 175.21 |
| C1 | 103.91 | 110.25 |
| C3 | 85.52 | 83.84 |
| C2 | 77.09 | 78.99 |
| C4 | 77.74 | 78.73 |
| C5 | 79.69 | 70.20 |
| —CH$_2$—O— | 69.69 | 68.68 |
| -(CH$_2$)$_n$- | 33.84; 31.31; 30.87; | 31.74; 31.31; 30.86; |
|  | 30.45; 30.33; 30.22; | 30.29; 30.24; 30.20; |
|  | 30.03; 29.72; 26.75; | 30.02; 29.71; 26.79; |
|  | 20.93 | 20.92 |
| IR | | |
| δCH$_2$ | 2960 | 2926, 2855 |
| γC=O | 1770 | 1785 |

EXAMPLE 8

Preparation of sodium 11-(perfluorooctyl)undecyl-β-D-glucofuranuronate

To 8 g (10.7 mmol) of 11-(perfluorooctyl)undecyl-6(3)-β-D-glucofuranuronolactone of Example 7 dissolved in 150 ml of 96% ethanol and maintained at 35° C. is added 2.86N sodium hydroxide solution dropwise until a pH in the region of 12 is obtained.

After stirring for 3 hours, the suspension is partially concentrated (to 50 ml). The precipitate formed is filtered off, washed with absolute ethanol (20 ml×2) and dried under vacuum.

4.15 g of sodium 11-(perfluorooctyl)undecyl-β-D-glucofuranuronate are recovered, i.e. a yield, calculated on the basis of the starting lactone, equal to 53%.

This compound has the following IR characteristics:

δCH$_2$: 2922, 2853 and γC=O: 1625

EXAMPLE 9

Preparation of 11-(perfluorooctyl)undecyl-6(3)-D-glucofuranuronolactone 7.4 g (42 mmol) of 6(3)-D-glucuronolactone (85, 145-0; Aldrich), 30 g (51 mmol) of 11-(perfluorooctyl)undecenol (Ceca S. A.), 70 ml (56.2 g) of diglyme and 0.8 g (54 µl; 8.3 mmol) of methanesulphonic acid are introduced into a 250 ml three-necked round-bottomed flask.

After 12 hours at 80° C. under a vacuum of 13.33 kPa (distillation of 10 ml of diglyme and water), the reaction medium is cooled to 25° C. After adding 90 ml of water, the mixture is neutralized with $NaHCO_3$ and is stirred vigorously for 10 minutes.

The pasty precipitate thus obtained is filtered off, drained and dissolved in 180 ml of diethyl ether.

After washing the organic phase with water (30 ml×2), drying with magnesium sulphate and concentration under vacuum, a residue containing a mixture of the α and β anomers of 11-(perfluorooctyl)undecenyl-D-glucofuranuronolactone is obtained. After separation by column chromatography (silica 230–400 mesh ASTM; eluent: 1/1 (v/v) diethyl ether/hexane-diethyl ether gradient), 19 g of the β anomer and 2 g of the α anomer are recovered, i.e. a yield, calculated on the basis of the starting lactone, equal to 60.6% and 6.4% respectively.

The characteristics of the α and β anomers are given below.

Melting point of the α anomer: 68–70° C.
Rf:
α anomer: 0.53 (Z form) and 0.46 (E form)
β anomer: 0.31 (Z form) and 0.24 (E form)

|  | α anomer | β anomer |
|---|---|---|
| | ¹H NMR | |
| CH=CH(1H) | 6.50–6.35; m 70% | 6.50–6.35; m 72% |
|  | 6.20–6.05; m 30% | 6.20–6.05; m 28% |
| CH=CH(1H) | 5.70–5.52; m 70% | 5.70–5.52; m 72% |
|  | 5.52–5.40; m 30% | 5.52–5.40; m 28% |
| H1 | 5.28 | 5.10 |
|  | $J_{H1H2} = 4.4$ | $J_{H1H2} < 1$ |
| H4 | 4.84; m | 5.01; m |
|  | $J_{H3H4} = 3.2$ | $J_{H4H5} = 5.8$ |
|  | $J_{H4H5} = 4.8$ | $J_{H4H3} = 4.9$ |
| H3 | 4.78; m | 4.87; d |
|  | $J_{H3H2} < 1$ | $J_{H3H2} < 1$ |
| H5 | 4.49; m | 4.35; m |
|  | $J_{H5OH} = 8$ | $J_{H5OH} = 8.4$ |
| H2 | 4.40; t | 4.45; m |
|  | $J_{H2OH} = 5.3$ |  |
| H1'a | 3.89; m | 3.68; m; alkyl chain |
| H1'b | 3.59; m | 3.42; m; alkyl chain |
| 2-OH | 3.08; d |  |
|  | $J_{H2OH} = 5.4$ |  |
| 5-OH | 2.68; d | 2.68; d |
|  | $J_{H5OH} = 8.5$ | ($J_{H5OH} = 5.3$) |
| H9'a(1H) | 2.35–2.25; m 30% | 2.40–2.10; m |
|  | 2.25–2.10; m 70% |  |
| H2'a, 2'b | (2H)1.65–1.58; m | (15H)1.65–1.20; m |
| H9'b, CH₂3', 8' | (13H) 1.45–1.30 |  |
| | ¹³C NMR | |
| C6 | 174.45 | 174.85 |
| CH=CH | 145.65–144.54– | 145.66–143.38–117.25– |
|  | 143.37–117.33– | 116.70–116.34–116.04 |
|  | 116.87–116.42 |  |
| C1 | 102.59 | 109.20 |
| C3 | 84.81 | 83.34 |
| C4 | 76.39 | 77.13 |
| C2 | 76.03 | 77.57 |
| C5 | 70.37 | 69.33 |
| C1' | 69.84 | 69.18 |
| C2', 9' | 32.07–26.03 | 32.07–25.94 |
| | IR | |
| $\delta CH_2$ | 2961 | 2927, 2856 |
| $\gamma C=O$ | 1771 | 1791 |

EXAMPLE 10

Preparation of sodium 11-(perfluorooctyl) undecenyl-β-D-glucofuranuronate

To 0.241 g (0.33 mmol) of 11-(perfluorooctyl)undecyl-6 (3)-β-D-glucofuranuronolactone of Example 9 dissolved in 2 ml of absolute ethanol is added 0.11 ml of 2.86N sodium hydroxide solution.

After stirring for 2 hours at 25° C., the precipitate formed is filtered off, washed with cold absolute ethanol (5 ml×2) and dried under vacuum (2.4 kPa; 40° C.).

160 mg of sodium 11-(perfluorooctyl)-undecenyl-β-D-glucofuranuronate (mixture of the Z and E forms) are recovered, i.e. a yield, calculated on the basis of the starting lactone, equal to 63%.

This compound has the following IR characteristics:
$\delta CH_2$:2923, 2856; $\gamma C=O$: 1626; $\gamma$-OH: 3411

The surface tension and the CMC are respectively equal to 17.4 mN/m (control=16 mN/m) and 0.01 g/l.

EXAMPLE 11

Preparation of potassium 11-(perfluorooctyl) undecenyl-β-D-glucofuranuronate

The process is performed under the conditions of Example 10, modified in that the sodium hydroxide solution is replaced with 2N potassium hydroxide solution.

The potassium 11-(perfluorooctyl)undecenyl-β-D-glucofuranuronate obtained has a surface tension and a CMC which are respectively equal to 17.3 mN/m (control= 16 mN/m) and 0.01 g/l.

EXAMPLE 12

Preparation of 2-(perfluorohexyl)ethyl 2-(perfluorohexyl)ethyl-D-galacturonate 8.48 g (0.04 mmol) of D-galacturonic acid monohydrate (85, 728-9; Aldrich) and 87.4 g (0.24 mmol) of 2-(perfluorohexyl)ethanol (Foralkyl EOH 8; Ceca S. A.) are introduced into a 500 ml three-necked round-bottomed flask.

The mixture is brought to 80° C. under a vacuum of 8 kPa and, after stirring for 15 minutes, 0.38 g ($2 \times 10^{-3}$ mol) of para-toluenesulphonic acid monohydrate is added.

After 12 hours, the reaction medium is cooled to 20° C., neutralized with $NaHCO_3$ and filtered. After concentration under vacuum, the filtrate gives a brown oil containing the 2-(perfluorohexyl)ethyl 2-(perfluorohexyl)ethyl-D-galacturonate in the form of a mixture of the β-furanose anomer (predominant), the α-pyranose anomer and traces of the α-furanose and β-pyranose anomers.

The Rf values of the compounds of the mixture are as follows:

| furanose form: | α anomer = 0.54 |
|---|---|
|  | β anomer = 0.63 |
| pyranose form: | α anomer = 0.26 |
|  | β anomer = 0.33 |

This oil is fluidified by addition of 3 ml of ethyl acetate (final volume: 35 ml) and column-chromatographed (silica 230–400 mesh ASTM; eluent: 70/30 (v/v) ethyl acetate/ hexane). 9 g of the β-furanose form are recovered, i.e. a yield, calculated on the basis of the starting D-galacturonic acid, equal to 25.4%.

EXAMPLE 13

Preparation of 2-(perfluorooctyl)ethyl 2-(perfluorooctyl)ethyl-D-galacturonate 4.8 g (0.023 mol) of D-galacturonic acid monohydrate (85, 728-9; Aldrich), 19.1 g (0.042 mol) of 2-(perfluorooctyl)ethanol (Ceca S. A.), 40 ml of diglyme and 0.5 g ($5 \times 10^{-3}$ mol) of methanesulphonic acid are introduced into a 250 ml three-necked round-bottomed flask.

After 9 hours at 100° C. under a vacuum of 8 kPa, the reaction medium is cooled, neutralized with $NaHCO_3$ and filtered. The filtrate, to which are added 100 ml of deionized water, is stirred vigorously. The precipitate obtained is filtered off, washed (150 ml of deionized water and 150 ml of hot hexane) and dried under vacuum.

17 g of a powder containing 2-(perfluorooctyl)ethyl 2-(perfluorooctyl)ethyl-D-galacturonate which is a mixture of the 4 α and β anomers of the furanose and pyranose forms, the β-furanose form being predominant, are recovered.

This mixture has the following IR characteristics:
$\delta CH_2$: 2920; $\gamma C=O$: 1749; $\gamma$-OH: 3486

EXAMPLE 14

Preparation of 11-(perfluorooctyl)undecyl 11-(perfluorooctyl)undecyl-D-galacturonate 2.9 g (0.014 mol) of D-galacturonic acid monohydrate (85, 728-9; Aldrich), 21.2 g (0.036 mol) of 11-(perfluorooctyl)undecanol (Ceca S. A.), 40 ml of diglyme and 0.3 g ($3 \times 10^{-3}$ mol) of methanesulphonic acid are introduced into a 250 ml three-necked round-bottomed flask.

After 9 hours at 100° C. under a vacuum of 9.33 kPa, the reaction medium is cooled and neutralized with $NaHCO_3$. 120 ml of deionized water are added and the mixture is stirred vigorously for 30 minutes. The precipitate obtained is filtered off, washed with deionized water (100 ml×2) and with hot hexane (100 ml×2) and dried under vacuum.

17 g of a precipitate containing 11-(perfluorooctyl)undecyl 11-(perfluorooctyl)undecyl-D-galacturonate are recovered, i.e. a yield, calculated on the basis of the starting D-galacturonic acid, equal to 75%.

The precipitate is a mixture of the 4 α and β anomers of the furanose and pyranose forms, the IR characteristics of which are as follows:
$\delta CH_2$: 2923, 2853; $\gamma C=O$: 1747; $\gamma$-OH: 3442

EXAMPLE 15

Preparation of 11-(perfluorooctyl)undecenyl 11-(perfluorooctyl)undecenyl-D-galacturonate 3.6 g (0.017 mol) of D-galacturonic acid monohydrate (85, 728-9; Aldrich), 26.2 g (0.045 mol) of 11-(perfluorooctyl)undecenol (Ceca S. A.), 40 ml of diglyme and 0.4 g ($4 \times 10^{-3}$ mol) of methanesulphonic acid are introduced into a 250 ml three-necked round-bottomed flask.

After 8 hours at 90° C. under a vacuum of 9.33 kPa, the reaction medium is neutralized with $NaHCO_3$. 150 ml of deionized water are added and the mixture is stirred vigorously for 30 minutes. The precipitate obtained is filtered off, washed with deionized water (100 ml×3) and with hot hexane (100 ml×3).

17 g of 11-(perfluorooctyl)undecenyl 11-(perfluorooctyl)undecenyl-D-galacturonate are recovered, i.e. a yield, calculated on the basis of the starting D-galacturonic acid, equal to 75%.

This compound is dissolved in 5 ml of ethyl acetate and filtered on a column of silica (230–400 mesh ASTM; eluent: ethyl acetate). 10 g of a very viscous orange-coloured oil corresponding to a mixture of the 4 α and β isomers of the furanose and pyranose forms are recovered (yield: 44%).

The IR characteristics of the mixture obtained are as follows:
$\delta CH_2$: 2932, 2858; $\gamma C=O$: 1740; $\gamma$-OH: 3391

EXAMPLE 16

A shampoo is prepared by mixing together the following compounds (in g):

| | |
|---|---|
| Compound according to Example 2 | 5 |
| Compound according to Example 12 | 1 |
| Sodium lauryl ether sulphate (Rewopol N 3.28; Schering S.A.) | 40 |
| Cocoamidopropylbetaine (Rewoteric AMB 13; Schering S.A.) | 2 |
| Alkyl polyglucoside 1200 (Plantaren 1200; Henkel) | 2 |
| Sodium chloride | 1 |
| Preserving agent (Phenonip; Nipa Laboratories) | 0.1 |
| Fragrance (Fougere 10105, water-soluble 337 201; Laserson and Sabetay) | 0.2 |
| Demineralized water qs 100 | |

EXAMPLE 17

A conditioner is prepared by mixing together the following compounds (in g):

| | |
|---|---|
| Compound according to Example 5 | 2 |
| Merquat 280* (Merck) | 5 |
| Preserving agent (Phenonip; Nipa Laboratories) | 0.1 |
| Fragrance (⅓ vanilla 27800, water-soluble 008201; ⅔ fougère 10105, water-soluble 337201; Laserson and Sabetay) | 0.1 |
| Demineralized water qs 100 | |

*copolymer of dimethyldialkylammonium chloride and acrylic acid as an aqueous 35% solution.

The preceding examples can be repeated with similar success by substituting the generically or specifically described reactants and/or operating conditions of this invention for those used in the preceding examples.

The entire disclosure of all applications, patent and publications, cited above, and of corresponding French application 96/07693, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

We claim:

1. A compound of one of the formulae Ia, Ib or II (Ia)

$$\text{structure with } COOR_2, O, HO, OR_1, HO, OH$$

-continued

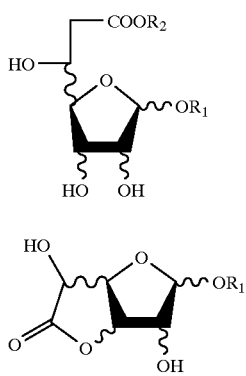

in which:

R$_1$ represents a saturated or unsaturated, linear or branched fluoroalkyl radical containing 4 to 46 carbon atoms;

R$_2$ represents H, R$_1$ as defined above, an alkali metal or alkaline-earth metal, or a quaternary ammonium of formula:

in which R$_3$, R$_4$, R$_5$ and R$_6$, which may be identical or different, represent H or a C$_1$–C$_6$ alkyl or hydroxyalkyl radical.

2. A compound according to claim 1, wherein R$_1$ has the formula:

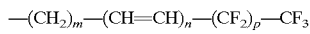

in which:

m is between 2 and 22, n is equal to 0 or 1, p is between 1 and 21.

3. A compound according to claim 1, selected from the group consisting of fluoroalkyl-6(3)-glucofuranuronolactone, fluoroalkyl-6(3)-annofuranuronolactone, fluoroalkyl-6(3)-idofuranuronolactone or fluoroalkyl-6(3)-gulofuranuronolactone.

4. A process for the preparation of the compounds according to claim 1, comprising:

a. reaction of a flycosiduronic acid or of a glycosiduronolactone with an alcohol of formula R$_1$OH in which R$_1$ represents a saturated or unsaturated linear or branched fluoroalkyl radical containing from 4 to 46 carbon atoms, in order to form the fluoroalkyl fluoroalkylglycosiduronate or the fluoroalkylglycosiduronolactone;

b. optionally, basification to form the fluoroalkylglycosiduronic acid salt, and c. optionally, acidification to form fluoroalkylglycosiduronic acid.

5. A process according to claim 4, wherein the glycosiduronic acid is a uronic acid containing 5 or 6 carbon atoms.

6. A process according to claim 5, wherein the acid is glucuronic acid, galacturonic acid, mannuronic acid, iduronic acid or guluronic acid.

7. A process according to claim 4, wherein the glycosiduronolactone is chosen from lactone of a uronic acid containing 5 or 6 carbon atoms.

8. A process according to claim 7, wherein the glycosiduronolactone is 6(3)-glucuronolactone, 6(3)-mannuronolactone, 6(3)-guluronolactone or 6(3)-iduronolactone.

9. A method for improving the surfactant properties of a composition which comprises adding to the composition a compound according to claim 1.

10. The method of claim 9, wherein the composition is a shampoo, conditioner or other hair composition, a beauty milk, a foam bath, an oral hygiene composition or another cosmetic cream or ointment.

* * * * *